(12) United States Patent
Oh et al.

(10) Patent No.: US 7,380,467 B2
(45) Date of Patent: Jun. 3, 2008

(54) BOND INTEGRITY TOOL

(75) Inventors: Chong T. Oh, Lexington Park, MD (US); William E. Farrell, Avenue, MD (US); William T. Jacoby, Lusby, MD (US); Bernard W. Baird, Avenue, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 221 days.

(21) Appl. No.: 11/417,287

(22) Filed: May 1, 2006

(65) Prior Publication Data

US 2007/0274641 A1 Nov. 29, 2007

(51) Int. Cl.
*G01N 3/04* (2006.01)

(52) U.S. Cl. ............................ 73/827; 73/831; 73/833; 73/856

(58) Field of Classification Search .................. 73/761, 73/862, 827, 831, 833, 856, 857, 862.393
See application file for complete search history.

(56) References Cited

U.S. PATENT DOCUMENTS

| 4,103,540 | A  | * | 8/1978  | McLaughlin ................ 73/831 |
| 5,664,467 | A  | * | 9/1997  | Breeze ........................ 81/114 |
| 5,997,012 | A  | * | 12/1999 | Brian ......................... 279/43.5 |
| 6,289,741 | B1 | * | 9/2001  | Ghetzler et al. ............... 73/827 |
| 6,766,698 | B1 | * | 7/2004  | Robinson et al. .............. 73/856 |
| 2005/0053423 | A1 | * | 3/2005 | Doubler et al. ........... 403/374.3 |

\* cited by examiner

*Primary Examiner*—Edward Lefkowitz
*Assistant Examiner*—Punam Patel
(74) *Attorney, Agent, or Firm*—Mark O. Glut

(57) ABSTRACT

The present invention is directed to a bond integrity tool, which includes a shoulder housing, a collar shaft, and an end cap. The collar shaft has a neck portion and a mouth portion. The neck portion is disposed within the shoulder housing, and the mouth portion is able to grip a test piece. The end cap communicates with the neck portion, such that when the end cap is initiated the end cap applies force on the shoulder housing, which in turn applies force on the collar shaft, which grips the test piece such that the bond integrity between the test piece and a surface may be tested.

12 Claims, 5 Drawing Sheets

BOND INTEGRITY TOOL

STATEMENT OF GOVERNMENT INTEREST

The invention described herein may be manufactured and used by or for the Government of the United States of America for governmental purposes without payment of any royalties thereon or therefor.

BACKGROUND

The present invention relates to a bond integrity tool. More specifically, but without limitation, the present invention relates to a bond integrity tool that is used to verify the adhesion and bonding integrity of a contact memory button to a variety of surfaces.

A contact memory button may be defined, but without limitation, as a button like memory storage device or as a battery-free read/write electronic data storage device designed to perform in extreme operating environments associated with military, aerospace, utility, transportation, and industrial applications. The contact memory button is typically attached, but without limitation, to an aircraft, a component, a platform or any type of surface. The purpose of the contact memory button is typically, but without limitation, to store or gather data. To properly function the contact memory button must be properly adhered to a surface and must be checked so that the contact memory button will stay adhered to the surface. In typical U.S. Navy applications, the contact memory button is adhered or bonded to a surface via an epoxy adhesive, and must meet certain adhesion/bonding requirements.

Thus, there is a need in the art to provide a bond integrity tool that can adequately check the bonding integrity of the contact memory button and other devices to a variety of surfaces.

SUMMARY

The present invention is directed to a bond integrity tool, which includes a shoulder housing, a collar shaft, and an end cap. The collar shaft has a neck portion and a mouth portion. The neck portion is partially disposed within the shoulder housing, and the mouth portion is able to grip a test piece. The end cap communicates with the neck portion such that when initiated the end cap applies force on the shoulder housing, which in turn applies force on the collar shaft which grips the test piece such that the bond integrity between the test piece and a surface may be tested.

It is a feature of the invention to provide a bond integrity tool that can adequately check the bonding integrity of a test piece to a variety of surfaces.

It is a feature of the invention to provide a bond integrity tool that is compact, convenient and easy to use. The bond integrity tool can also be used in tight spaces.

DRAWINGS

These and other features, aspects and advantages of the present invention will become better understood with reference to the following description and appended claims, and accompanying drawings wherein:

DESCRIPTION

Figure 1:
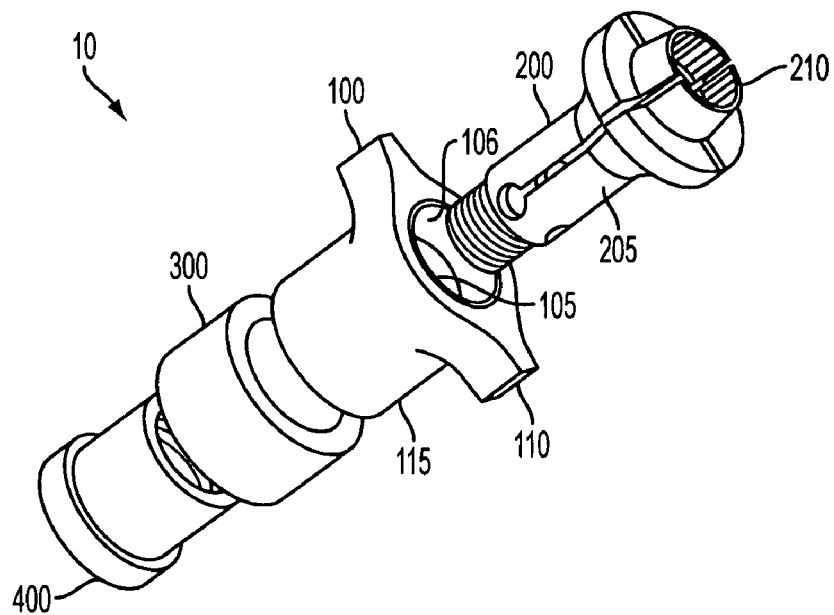
FIG. 1 is an exploded perspective view of an embodiment of the bond integrity tool.
Figure 2:
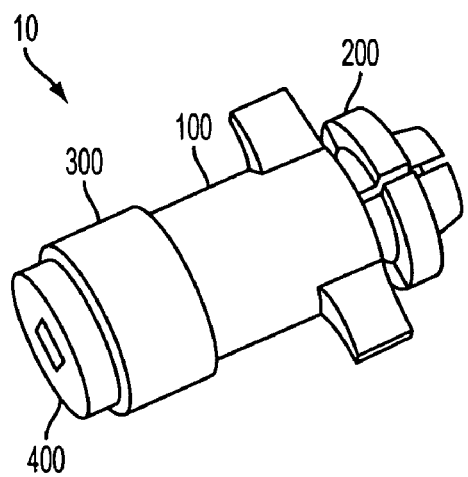
FIG. 2 is a perspective view of an embodiment of the bond integrity tool.

The preferred embodiment of the present invention is illustrated by way of example below and in FIGS. 1-6. As seen in FIGS. 1 and 2, the preferred embodiment of the bond integrity tool 10 includes a shoulder housing 100, a collar shaft 200, a housing sleeve 300, and an end cap 400. The housing sleeve 300 abuts the shoulder housing 100. The collar shaft 200 has a neck portion 205 and a mouth portion 210. The neck portion 205 is partially disposed within the shoulder housing 100, and the mouth portion 210 is able to grip a test piece (particularly a contact memory button). The end cap 400 communicates with the neck portion 205, while the housing sleeve 300 is disposed over a portion of the end cap 400.

Figure 3A:
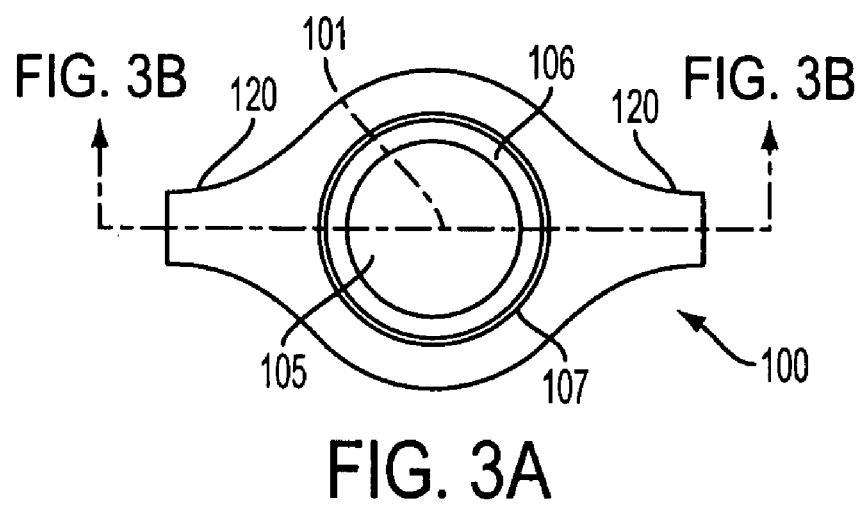
FIG. 3A is a top view of an embodiment of the shoulder housing.
Figure 3B:
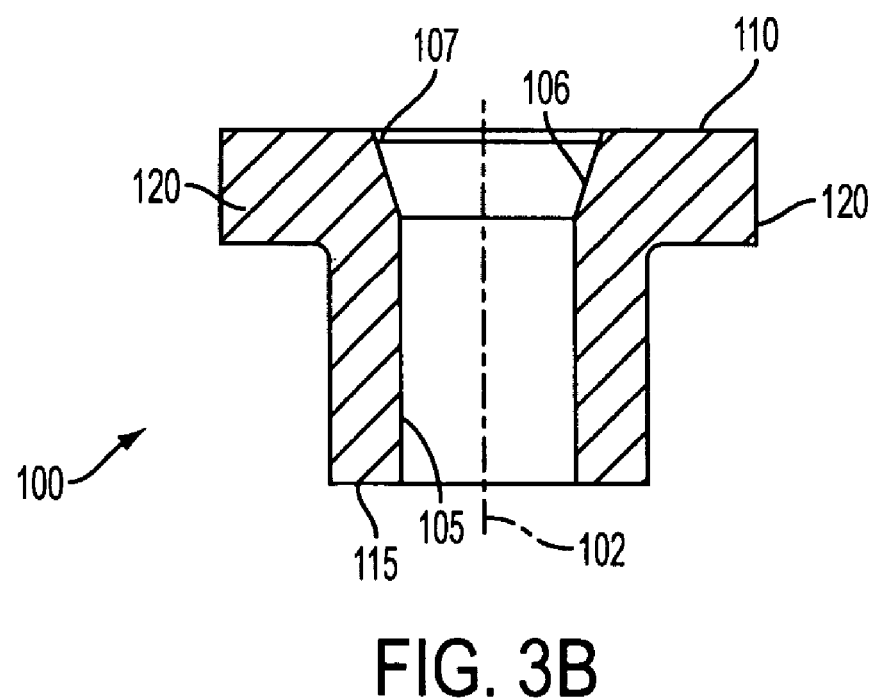
FIG. 3B is a cross-section taken through section 3B of FIG. 3A.

As seen in FIGS. 1, 3A and 3B, the shoulder housing 100 includes a shoulder housing bore 105. The shoulder housing bore 105 may extend through the entire axial length of the shoulder housing 100. However, in the preferred embodiment, the shoulder housing 100 also includes a shoulder housing tapered bore 106 and a lip 107. The axis of the shoulder housing tapered bore 106 corresponds to the axis of the shoulder housing bore 105 and to the axis of the lip 107. The shoulder housing 100 may include a first shoulder housing end 110 and a second shoulder housing end 115. The shoulder housing bore 105 extends from the second shoulder housing end 115 to the shoulder housing tapered bore 106. The shoulder housing tapered bore 106 extends from the shoulder housing bore 105 to the lip 107. The lip 107 extends from the shoulder housing tapered bore 106 to the first shoulder housing end 110.

In the preferred embodiment, the shoulder housing 100 includes two projections 120 disposed at or near the first shoulder housing end 110. The shoulder housing 100 may be substantially cylindrical with the two projections 120 on opposite sides from each other. In the preferred embodiment, the shoulder housing 100 is substantially symmetrical along the shoulder housing centerline 102. In the preferred embodiment, the shoulder housing 100 is manufactured from aluminum, specifically 6061-T6 Aluminum.

In the preferred embodiment, as seen in FIGS. 1, 4A, 4B, and 4C, the mouth portion 210 of the collar shaft 200 includes a flange portion 213 and a collet 209. Additionally, the neck portion 205 of the collar shaft 200 includes a sloped portion 206, a shaft portion 207 and a threaded portion 208. The collet 209, the flange portion 213, the sloped portion 206, the shaft portion 207 and the threaded portion 208 may all be substantially axially aligned and may all have an outer diameter that is substantially circular. The collet 209 and the threaded portion 208 are disposed on opposite ends of the collar shaft 200. The flange portion 213 is disposed between the collet 209 and the sloped portion 206 of the neck portion 205. The sloped portion 206 curves or slants inwardly toward the shaft portion 207 and away from the flange portion 213. The shaft portion 207 extends from the sloped portion 206 to the threaded portion 208. The shaft portion 207 may also include an indentation 217 at its end closest to the threaded portion 208. The indentation 217 may wrap around the outer diameter of the shaft portion 207. The collar shaft 200 may also include a collar shaft bore 220. The collar shaft bore 220 may run through the entire axial length of the collar shaft 200. The shoulder housing 100, via the shoulder housing bore 105, the shoulder housing tapered bore 106, and lip 107 accepts the threaded portion 208, the shaft portion 207, and the sloped portion 206. The threaded portion 208 may be screwed into corresponding threads 414 located within the end cap 400.

Figure 4A:
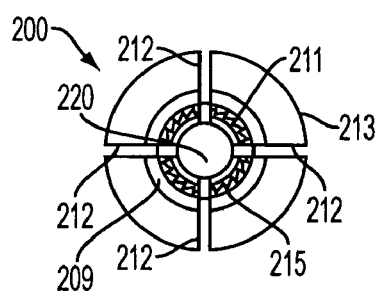
FIG. 4A is a top view of an embodiment of the collar shaft.
Figure 4B:
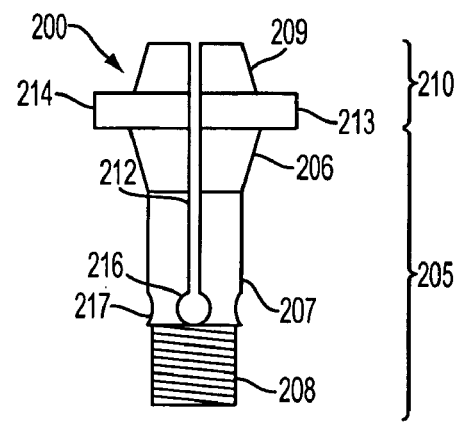
FIG. 4B is a side view of an embodiment of the collar shaft.

The collar shaft 200 may include four grooves 212. As shown in FIG. 4A, the four grooves 212 are spaced at approximately ninety degree intervals around the circumference of the collar shaft 200. The grooves 212 extend radially through the collet 209, the flange portion 213, the sloped portion 206 and the shaft portion 207. As seen in FIG. 4B, at the axial end of the grooves 212 at or about the shaft portion 207 end nearest the threaded portion 208, the four grooves 212 turn into four circular bores 216. The circular bores 216 extend radially through the shaft portion 207. The circular bores 216 are spaced at about 90 degree intervals around the circumference of the shaft portion 207.

Figure 4C:
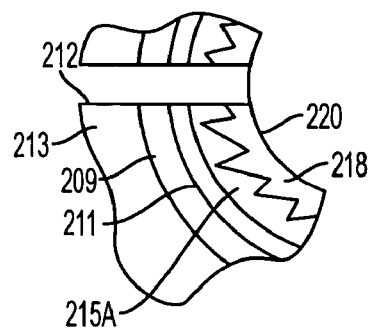
FIG. 4C is an enlargement showing a portion of the teeth 215A of FIG. 4A.

Disposed within the inner diameter 211 of the collet 209 is a gripping surface 215 for gripping a test piece, particularly a contact memory button. As seen in FIG. 4C, the gripping surface 215 may be teeth 215A disposed on the inner diameter 211 of the collet 209. The teeth 215A may be disposed in a circular configuration along the inner diameter 211 of the collet 209. In the preferred embodiment, the teeth 215A are standing ridges that axially extend throughout the inner diameter 211 of the collet 209. As seen in FIG. 4C, the flange portion 213 may include a flange ledge 218. The flange ledge 218 is disposed at the inner diameter of the flange portion 213 and extends inwardly past the teeth 215A.

The outer edge 214 of the flange portion 213 may be knurled. In the preferred embodiment of the invention, the outer edge 214 is diamond knurled. In the preferred embodiment, the collar shaft 200 is manufactured from 4130 steel.

Figure 5A:
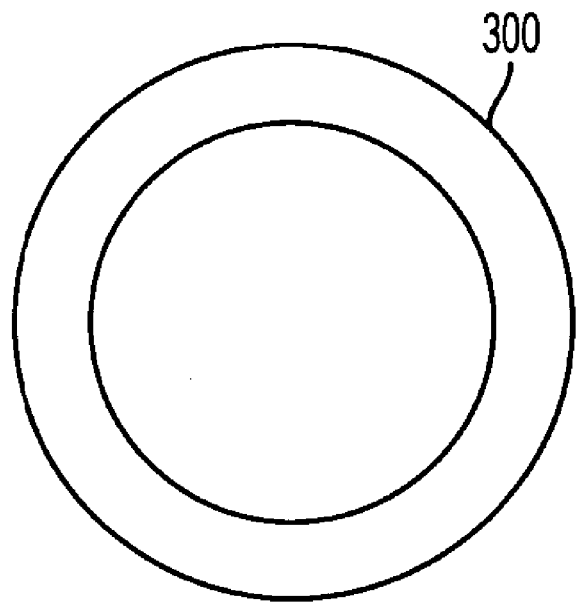
FIG. 5A is a top view of an embodiment of the housing sleeve.
Figure 5B:
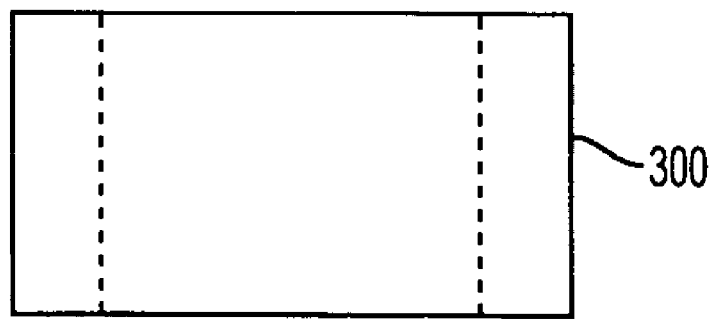
FIG. 5B is a side view of an embodiment of the housing sleeve.
Figure 6A:
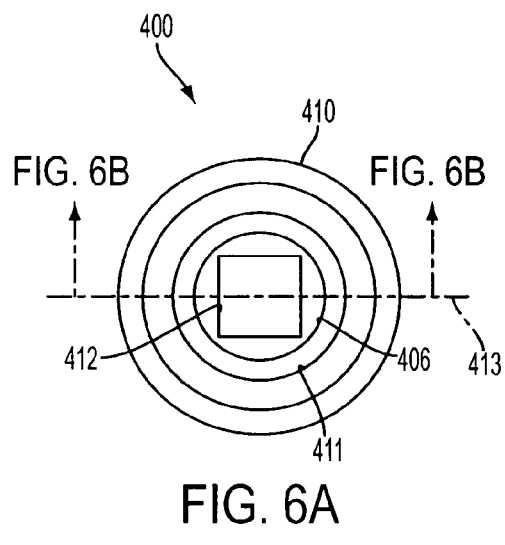
FIG. 6A is a top view of an embodiment of the end cap.
Figure 6B:
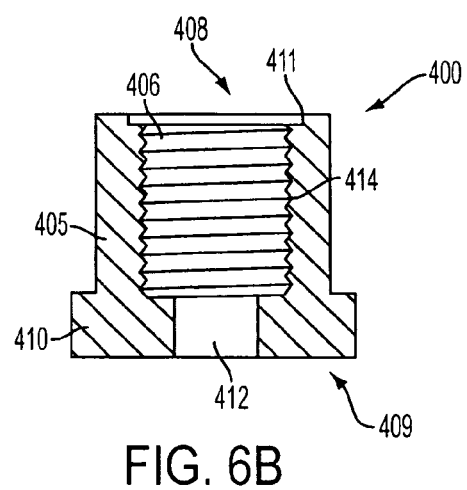
FIG. 6B is a cross section taken through section 6B of FIG. 6A.
Figure 6C:
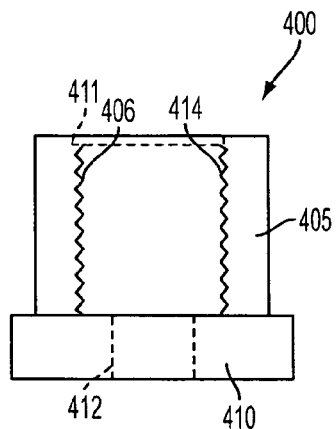
FIG. 6C is a side view of an embodiment of the end cap.

As seen in FIGS. 1, 5A and 5B, in the preferred embodiment, the housing sleeve 300 is an annulus, a hollowed cylinder, or a ring that abuts the shoulder housing 100 and can envelop or cover a portion of the end cap 400. In the preferred embodiment, the housing sleeve 300 is manufactured from 6061-T6 Aluminum and is anodized black.

As seen in FIGS. 1, 6A, 6B and 6C, in the preferred embodiment the end cap 400 includes a cylinder portion 405 and a cap flange portion 410. The housing sleeve 300 may envelop or cover the cylinder portion 405. The cylinder portion 405 has an end cap bore 406 that may include corresponding threads 414 such that the end cap bore 406 can accept and correspond to the threaded portion 208 of the collar shaft 200. The end cap bore 406 axially extends through the cylinder portion 405 ending at the cap flange portion 410, whereby the end cap bore 406 communicates with a flange aperture 412. The end cap bore 406 and the flange aperture 412 may be substantially axially aligned. The flange aperture 412 axially extends through the cap flange portion 410 and may have a cross section that has a polygonal shape. The preferred embodiment of the cross section of the flange aperture 412 has a square shape; however, the flange aperture 412 cross section may be any shape that corresponds to the driving spindle of a torque wrench. The outer diameter of the end cap 400 may have a substantially circular shape. The end cap 400 may include a cap first end 408 and a cap second end 409. The cylinder portion 405 may be located at the cap first end 408, while the flange portion 410 may be located at the cap second end 409. At the cap first end 408 there may be an end cap counter bore 411, which extends to the end cap bore 406. The axis of the end cap counter bore 411 may correspond to the axis of the end cap bore 406. The end cap 400 way be substantially cylindrical in shape and substantially symmetrical about its centerline 413.

The contact memory button (i.e. the test piece) is typically on a surface located on a component, an aircraft or a type of test piece platform. A test piece platform may be defined, but without limitation, as any type of material, area or item wherein a test piece is placed or disposed. In operation, the present invention is assembled as shown in FIGS. 1 and 2, and the collet 209 is placed onto the test piece (in particular, the head of the contact memory button), such that the gripping surface 215 is in contact with the test piece. The test piece may be in contact with flange ledge 218. By spinning the cap flange portion 410, the end cap 400 (via the corresponding threads 414) is tightened to the threaded portion 208 of the collar shaft 200 such that the cylinder portion 405 of the end cap 400 presses against the shoulder housing 100 which in turn presses against the sloped portion 206 of the collar shaft 200 which in turn tightens the collet 209 around the test piece. While holding the shoulder housing 100, specifically holding one or both of the projections 120, a torque wrench set at a desired torque is connected to the end cap 400, specifically connected via the flange aperture 412. The collet 209 is then tightened around the test piece until the desired testing torque is obtained. The resistance or torque is provided by the gripping surface 215. Once the desired torque is obtained, the shoulder housing 100 is released and the desired testing torque is applied to the test piece to certify the bonding integrity between the test piece and surface. If the test piece remains bonded to the surface the bond has proper or adequate bonding integrity.

When introducing elements of the present invention or the preferred embodiment(s) thereof, the articles "a," "an," "the," and "said" are intended to mean there are one or more of the elements. The terms "comprising," "including," and "having" are intended to be inclusive and mean that there may be additional elements other than the listed elements.

Although the present invention has been described in considerable detail with reference to certain preferred embodiments thereof, other embodiments are possible. Therefore, the spirit and scope of the appended claims should not be limited to the description of the preferred embodiment contained herein.

What is claimed is:

1. A bond integrity tool, comprising:
   a shoulder housing;
   a collar shaft, the collar shaft comprising a neck portion, a mouth portion, and four grooves disposed at ninety degree intervals around the circumference of the collar shaft, the four grooves extending through a portion of the collar shaft, the neck portion partially disposed within the shoulder housing, the mouth portion including an inner diameter with a gripping surface disposed within the inner diameter, the mouth portion able to grip a test piece; and an end cap, the end cap communicating with the shoulder housing and the neck portion such that when the end cap is initiated the end cap applies force on the shoulder housing, which in turn applies force on the collar shaft which via the mouth portion grips the test piece such that the bond integrity between the test piece and a surface may be tested.

2. A bond integrity tool, comprising:

a shoulder housing, the shoulder housing including a shoulder housing bore;

a housing sleeve, the housing sleeve abuts the shoulder housing;

a collar shaft, the collar shaft includes a neck portion and a mouth portion, the neck portion partially disposed within the shoulder housing via the shoulder housing bore, the mouth portion able to grip a test piece, the mouth portion includes an inner diameter with a gripping surface disposed within the inner diameter, the collar shaft includes four grooves extending through the mouth portion and a portion of the neck portion; and an end cap, the housing sleeve disposed over a portion of the end cap, the end cap communicating with the shoulder housing and the neck portion, such that when the end cap is initiated the end cap applies force on the shoulder housing, which in turn applies force on the mouth portion which via the gripping surface grips the test piece such that the bond integrity between the test piece and a surface may be tested.

3. The bond integrity tool of claim 2, wherein the neck portion of the collar shaft includes a sloped portion, a shaft portion and a threaded portion, the end cap includes a threaded end cap bore, such that the threaded portion and the threaded end cap bore are corresponding.

4. The bond integrity tool of claim 3, wherein the gripping surface is teeth.

5. The bond integrity tool of claim 3, wherein the gripping surface includes teeth disposed in a circular configuration.

6. The bond integrity tool of claim 5, wherein the grooves extend through the sloped portion and the shaft portion, the grooves include circular bores located at an end of the grooves closest to the threaded portion of the collar shaft.

7. A bond integrity tool, comprising:

a shoulder housing, the shoulder housing includes a shoulder housing bore and a shoulder housing tapered bore;

a housing sleeve, the housing sleeve abutting the shoulder housing;

a collar shaft, the collar shaft includes a neck portion and a mouth portion, the neck portion disposed within the shoulder housing via the shoulder housing bore and the shoulder housing tapered bore, the mouth portion able to communicate with a test piece, the mouth portion includes an inner diameter with teeth disposed within the inner diameter, the collar shaft includes four grooves spaced at approximately ninety degree intervals around the circumference of the collar shaft, the grooves axially extending through a portion of the collar shaft; and an end cap, the end cap including a cylinder portion and a cap flange portion, the housing sleeve disposed over the cylinder portion of the end cap, the end cap communicating with the shoulder housing and the neck portion, such that when the end cap is initiated the cylinder portion of the end cap applies force on the shoulder housing, which in turn applies force on the mouth portion which via the teeth grips the test piece such that the bond integrity between the test piece and a surface may be tested.

8. The bond integrity tool of claim 7, wherein the cap flange portion of the end cap includes a flange aperture, the flange aperture is shaped to correspond to a torque wrench driving spindle.

9. The bond integrity tool of claim 8, wherein the neck portion of the collar shaft includes a sloped portion, a shaft portion and a threaded portion, the end cap comprising a threaded end cap bore, such that the threaded portion and the threaded end cap bore are corresponding.

10. The bond integrity tool of claim 9, wherein the mouth portion includes a flange portion and a collet, the collet and the threaded portion disposed on opposite ends of the collar shaft, the teeth disposed on the inner diameter of the collet.

11. The bond integrity tool of claim 10, wherein the flange portion is disposed between the collet and the sloped portion, the sloped portion extending from the flange portion toward the shaft portion, the shaft portion extending from the sloped portion toward the threaded portion.

12. The bond integrity tool of claim 11, wherein the collar shaft further includes a collar shaft bore extending axially through the collar shaft.

* * * * *